United States Patent [19]

Tanaka et al.

[11] Patent Number: 4,490,554

[45] Date of Patent: Dec. 25, 1984

[54] PROCESS FOR CRYSTALLIZING TRIMELLITIC ACID

[75] Inventors: Toru Tanaka; Masanori Hataya; Kazuo Tanaka, all of Kurashiki, Japan

[73] Assignee: Mitsubishi Gas Chemical Company, Inc., Tokyo, Japan

[21] Appl. No.: 454,595

[22] Filed: Dec. 30, 1982

[30] Foreign Application Priority Data

Jan. 23, 1982 [JP] Japan ................................. 57-9334

[51] Int. Cl.³ ............................................. C07C 51/43
[52] U.S. Cl. .................................... 562/486; 562/416; 562/417
[58] Field of Search .................. 562/486, 416, 417

[56] References Cited

U.S. PATENT DOCUMENTS

| | | | |
|---|---|---|---|
| 3,033,899 | 12/1957 | Knobloch et al. | 562/486 |
| 3,708,532 | 1/1973 | Ichikawa et al. | 562/486 |
| 4,346,232 | 8/1982 | Komatsu et al. | 562/416 |

Primary Examiner—Natalie Trousof
Assistant Examiner—Vera C. Clarke
Attorney, Agent, or Firm—Armstrong, Nikaido, Marmelstein & Kubovcik

[57] ABSTRACT

In crystallizing and separating trimellitic acid obtained by the oxidation of dimethylbenzaldehyde or its oxidation derivative with a molecular oxygen-containing gas in an aqueous solvent in the presence of a bromine ion or a bromine ion and a heavy metallic ion catalyst, a process for crystallizing trimellitic acid wherein the crystallization is carried out with at least two crystallization vessels connected in series, of which the first vessel is kept at a temperature of 40° to 130° C. and at a concentration of trimellitic acid of 20 to 60 wt. %.

2 Claims, No Drawings

PROCESS FOR CRYSTALLIZING TRIMELLITIC ACID

The present invention relates to a process for crystallizing and separating trimellitic acid obtained by the oxidation of dimethylbenzaldehyde or its oxidation derivative with a molecular oxygen-containing gas in an aqueous solvent.

Trimellitic acid is widely used as a raw material for alkyd resins, high-grade plasticizers and polyesters, and is a very useful substance. In order to use the acid as a raw material for these, however, a high-purity product is generally required, and even trace amounts of impurities should be removed.

As the conventionally well-known processes for producing trimellitic acid, there is a process in which pseudocumene is brought into contact with a molecular oxygen-containing gas in an acetic acid solvent in the presence of a cobalt/manganese/bromine type catalyst. Trimellitic acid thus produced is finally obtained as trimellitic acid anhydride by removing the solvent by distillation, passing the resulting aqueous solution through treatment steps such as extraction of impurities, recrystallization, adsorption, etc., and then dehydrating distillation. But the quality of trimellitic acid anhydride thus obtained is not sufficeint for these complicated treatments. As one reason for such complicated treatments being necessary, there is given difficulty in crystallization owing to the supersaturation phenomenon of trimellitic acid. That is to say, in order to obtain crude trimellitic acid in satisfactory yields from the reaction mixture by crystallization by cooling, long periods of time beyond expectation are necessary, and besides crystals obtained are fine. Even by solid/liquid separation, therefore, the recovered crystal contains large quantities of a mother liquor containing impurities in large amounts.

On the basis of the aforementioned behavior on crystallization of the aqueous trimellitic acid solution, the present inventors extensively studied the crystallization and separation of trimellitic acid obtained by oxidation in aqueous solvents for the purpose of searching for a crystallization rate economically applicable to an industrial scale as well as improving the particle size of crystal so as to facilitate the separation of trimellitic acid from the water-soluble catalyst component and impurities. As a result, it was found the effect of the supersaturation phenomenon is relatively low under a particular crystallization condition, whereby acceleration of crystallization rate as well as improvement of the particle size of crystal are achieved to obtain crude trimellitic acid crystals containing little mother liquor. The present invention was completed based on this finding.

According to the present invention, there are provided the following processes: In crystallizing and separating trimellitic acid obtained by the oxidation of dimethylbenzaldehyde or its oxidation derivative with a molecular oxygen-containing gas in an aqueous solvent in the presence of a bromine ion or a bromine ion and a heavy metallic ion catalyst, a process in which crystallization is carried out with at least two crystallization vessels connected in series, of which the first vessel is kept at a temperature of 40° to 130° C. and at a concentration of trimellitic acid of 20 to 60 wt. %, and a process in which 10 to 50% of the slurry solution from the final crystallization vessel of the above process is circulated to the first vessel.

By the term "dimethylbenzaldehyde or its oxidation derivative" used as a starting material for the production of trimellitic acid in the present invention, are meant substances which will finally turn trimellitic acid by oxidation. For example, there are given 2,4-dimethylbenzaldehyde, 3,4-dimethylbenzaldehyde, 2,4-dimethylbenzoic acid, 3,4-dimethylbenzoic acid, 4-methylphthalic acid, 2-methylterephthalic acid and the like. As the bromine ion used for oxidation, any of those generating a bromine ion under the reaction condition, for example hydrogen bromide, ammonium bromide, sodium bromide, manganese bromide and the like, may be used. As the heavy metallic ion, various heavy metals may be used. Of these, manganese and cerium are particularly preferred, and other ones such as nickel, chromium, molybdenum, iron, lead, tin, cobalt, niobium and the like may also be used.

In the crystallization process according to the present invention, it is necessary to use at least two, particularly two to four crystallization vessels connected in series, and crystallization is carried out by keeping the first crystallization vessel at a temperature of 40° to 130° C. and at a concentration of trimellitic acid of 20 to 60 wt. %. The term "the concentration of trimellitic acid in the crystallization vessel" referred to herein means the proportion, as expressed by weight %, of the sum of deposited trimellitic acid and dissolved one to the whole slurry solution, and it shows a concentration at the outlet for continuous-type crystallization vessels and a final concentration in vessel for batch-type crystallization vessels. When the crystallization temperature is lower than 40° C., the crystallization rate is slow, while when it is higher than 130° C., the solubility of trimellitic acid in water increases to make crystallization substantially impossible. When the concentration of trimellitic acid is less than 20 wt. %, it is difficult to obtain the crystal having a low liquor content in satisfactory yields within an economical period of residence time.

A higher concentration of the aqueous trimellitic acid solution makes it possible to obtain the crystal having a low liquor content in satisfactory yields within a shorter period of residence time. When the concentration is however more than 60 wt. %, the fluidity becomes markedly poor to make transportation of the slurry solution difficult.

As to the temperature of the second crystallization vessel and vessels following it, it is preferred to decrease by 5° to 60° C. below the temperature of the preceding vessel, but the temperature of the final crystallization vessel needs to be 0° C. or more.

The concentration of trimellitic acid in the second crystallization vessel and vessels following it need not be particularly limited, but generally, concentrations of about 40 to about 50 wt. %, as expressed in slurry concentration, are preferred in terms of transportation. For this purpose, when the trimellitic acid concentration of the first vessel is as high as 50 to 60%, since the slurry concentration increases by crystallization to make transportation gradually difficult, the slurry concentration is diluted to a transportable degree with addition of water. Contrary to this, when the trimellitic acid concentration of the first vessel is as low as about 20 to about 30%, it is necessary to remove water to make crystallization easy.

The total residence time from the first to final vessels is 0.5 to 10 hours, preferably 1 to 5 hours. The total residence time is a sum of the residence time in each vessel. When it is shorter than 0.5 hour, the growth of crystal is so insufficient that the crystal having a low liquor content is difficult to obtain. If it is made longer than 10 hours, the particle size does not change substantially, which is not therefore economical.

The residence time in each vessel needs not be the same, and it is within a range of 0.25 hour to 2.5 hours. The total number of crystallization vessels is preferably 2 to 4. When 10 to 50% of the slurry solution from the final crystallization vessel is circulated to the first one, the crystallization rate and the particle size of crystal are improved further more.

As the crystallization apparatus used in the present invention, cooling-type crystallizers and vacuum cooling-type crystallizers are preferred. As the former crystallizers, complete stirring-type crystallizers, oslo-type crystallizers, etc. are particularly preferred. As the latter crystallizers, slurry circulation-type crystallizers, magma circulation-type crystallizers are particularly preferred.

According to the present invention, trimellitic acid crystals having little impurity content and a large particle size can be obtained efficiently.

EXAMPLE 1

A reaction mixture having a trimellitic acid concentration of 30 wt. % and a $Mn^{2+}$ concentration of 0.35 wt. % obtained by the air-oxidation of dimethylbenzaldehyde in an aqueous solvent was heated to 100° C. to dissolve the acid, and sent to the first crystallization vessel (2-liter capacity), a complete mixing-type vessel equipped with a jacket, kept at 75° C. at a rate of 2 liter/hour by means of a metering pump.

The second crystallization vessel (2-liter capacity) kept at 55° C. was connected with the first one by a connecting pipe, and the third crystallization vessel (2-liter capacity) kept at 20° C. was connected with the second one.

The slurry was withdrawn from the third crystallization vessel at a rate of 2 liter/hour by means of a tube pump. Under the condition that the residence time in each vessel be 1 hour and the total residence time be 3 hours, crystallization was carried out with addition of 30 g of trimellitic acid as seed crystal to the first crystallization vessel. When a sufficient stationary state was reached after 6 hours' passage, 1500 g of a slurry of trimellitic acid having an average crystal particle size of 60 to 65μ was collected. This slurry was then centrifuged batchwise for 3 minutes with a centrifugal effect of 390 G.

The yield of the trimellitic acid wet cake obtained was 526 g, and that of the first mother liquor was 974 g. Thereafter, 526 g of the cake was turned into a slurry with addition of 500 g of cold water (12° C.) and centrifuged for 5 minutes with a centrifugal effect of 390 G.

The yield of the trimellitic acid wet cake obtained was 519 g, and that of the second mother liquor was 507 g.

519 Grams of the cake obtained was then allowed to stand overnight in a dryer kept at 70° C. to obtain 412 g of a dry trimellitic acid crystal.

The trimellitic acid and manganese were analyzed by gas chromatography and atomic flame spectrophotometric method, respectively. As a result, it was found that the purity of the dry trimellitic acid crystal was 98.3 wt. %; the manganese content of the crystal 250 ppm; the trimellitic acid concentration of the first mother liquor 3.20 wt. %; and that of the second of one was 2.51 wt. %.

The water content of the crystal based on the dry cake was 26.0%, the yield of crude trimellitic acid was 91.6% and the manganese loss due to attachment to crystal was 1.9%.

EXAMPLE 2

Crystallization was carried out in the same manner as in Example 1 except that a reaction mixture having a trimellitic acid concentration of 41 wt. % and a $Mn^{2+}$ concentration of 0.50 wt. % obtained by the air-oxidation of dimethylbenzaldehyde in an aqueous solvent was placed in a pressure-proof closed vessel and maintained at 115° C. under a nitrogen pressure of 2 kg/cm² to dissolve the acid, the resulting solution was supplied at a rate of 2 liter/hour to the first crystallization vessel (2-liter capacity) kept at 70° C. by means of a solenoid valve operated by a timer, and that the temperature of the second crystallization vessel was kept at 30° C.

Crystallization was continuously carried out for 4 hours after adding 20 g of trimellitic acid as seed crystal to the first crystallization vessel, during which the residence time in the first and second vessels each was made 1 hour and the total residence time 2 hours. Thereafter, 1500 g of a slurry of trimellitic acid having an average crystal particle size of 60 to 65μ was collected.

This slurry was centrifuged batchwise for 5 minutes with a centrifugal effect of 390 G at a stationary state.

The yield of the trimellitic acid wet cake obtained was 736 g, and that of the first mother liquor was 764 g.

Further, the acid cake obtained was turned into a slurry with addition of 600 g of cold water (12° C.) and centrifuged for 5 minutes with a centrifugal effect of 390 G.

The yield of the trimellitic acid wet cake obtained was 714 g, and that of the second mother liquor was 622 g.

714 Grams of the acid cake obtained was dried and weighed to obtained 580 g of a crystal.

The purity of the dry trimellitic acid was 98.0 wt. %; the manganese content of the acid 260 ppm; the trimellitic acid concentration of the first mother liquor 3.81 wt. %; and that of the second one was 2.80 wt. %.

The water content of the crystal based on the dry cake was 23.1%, the yield of trimellitic acid was 94.3% and the manganese loss due to attachment to crystal was 2.0%.

COMPARATIVE EXAMPLE 1

Crystallization was carried out under the same condition as in Example 1 except that a reaction mixture having a trimellitic acid concentration of 16.6 wt. % and a $Mn^{2+}$ concentration of 0.35 wt. % was used. Thereafter, 1500 g of a slurry of trimellitic acid having an average crystal particle size of 40 to 50μ was collected and centrifuged. As a result, the yield of the trimellitic acid wet cake obtained was only 63 g, and that of the first mother liquor was 1437 g.

The separated cake was then turned into a slurry with addition of 50 g of cold water (12° C.) and centrifuged similarly.

The yield of the trimellitic acid wet cake obtained was 60.8 g, and that of the second mother liquor was 52 g.

The trimellitic acid cake after drying was weighed, and it was found that the yield was 33.8 g, the purity was 97.2% and the manganese content was 230 ppm. Further, the trimellitic acid concentration of the first mother liquor was 14.9 wt. %, and that of the second mother liquor was 3.35 wt. %.

The water content of the crystal based on the dry cake was 79.9%, the yield of trimellitic acid was only 13.6% and the manganese loss due to attachment to crystal was 0.2%.

COMPARATIVE EXAMPLE 2

Crystallization was carried out under the same condition as in Example 1 except that the temperature of the first, second and third crystallization vessels was 35° C., 30° C. and 20° C., respectively. Thereafter, 1500 g of a slurry of trimellitic acid having an average crystal particle size of 40 to 50μ was collected and centrifuged. As a result, the yield of the trimellitic acid wet cake obtained was 756 g, and that of the first mother liquor was 744 g.

The separated cake was then turned into a slurry with addition of 500 g of cold water (12° C.) and centrifuged similarly.

The yield of the trimellitic acid wet cake obtained was 705 g, and that of the second mother liquor was 551 g.

The trimellitic acid cake after drying was weighed, and it was found that the yield was 401 g.

The purity of the dry trimellitic acid crystal was 96.5%; the manganese content of the acid 2320 ppm; the trimellitic acid concentration of the first mother liquor was 4.91 wt. %; and that of the second one was 4.10 wt. %.

The water content of the crystal based on the dry cake was 75.8%, the yield of crude trimellitic acid was 89.1% and the manganese loss due to attachment to crystal was 17%.

EXAMPLE 3

A reaction mixture having a trimellitic acid concentration of 30 wt. % and a $Mn^{2+}$ concentration of 0.35 wt. % obtained by the air-oxidation of dimethylbenzaldehyde in an aqueous solvent was heated to 100° C. to dissolve the acid, and sent to a crystallization vessel at a rate of 2 liter/hour by means of a metering pump. Three complete mixing-type crystallization vessels (2-liter capacity) were connected in series by a connecting pipe.

Using the outer jacket mounted on each crystallization vessel, the temperature and flow amount of cooling water passing through the jacket were regulated so that the temperature of the first, second and third vessels was 75° C., 55° C. and 20° C., respectively.

The slurry was withdrawn from the third vessel at a rate of 2 liter/hour by means of a tube pump, and 0.24 liter/hour (recycle rate, 12%) of the slurry was circulated to the first vessel. When a sufficient stationary state was considered to be reached after 6 hours' passage, 1510 g of the trimellitic acid slurry was collected.

This slurry was fed to a centrifuge, and after the number of rotations became constant (390 G), centrifuged batchwise for 3 minutes.

The yield of the trimellitic acid wet cake (first cake) obtained was 514 g, and that of the first mother liquor was 970 g. Thereafter, 514 g of this cake was turned into a slurry with addition of 500 g of cold water (12° C.) and centrifuged in the same manner as above to obtain 505 g of the second wet cake and 495 g of the second mother liquor. The yield of the dry trimellitic acid was 417.5 g, and the dry acid had a purity of 98.2% and a manganese content of 260 ppm.

The yield of trimellitic acid was 92.2%; the manganese loss, 2.1%; the water content of the first and second cakes, 23% and 21% respectively; and the average particle size of the crystal was 65μ.

EXAMPLE 4

Experiment was carried out with completely the same crystallization apparatus and crystallization condition as in Example 3 except that the slurry from the third crystallization vessel was circulated to the first one at a rate of 0.460 liter/hour (recycle rate, 23%).

After 6 hours' passage, 1493 g of the trimellitic acid slurry was collected. Thus slurry was then fed to a centrifuge and treated by the same operation as in Example 3 to obtain 496 g of the trimellitic acid wet cake (first cake) and 985 g of the first mother liquor.

Thereafter, this first cake was turned into a slurry with addition of 500 g of cold water (12° C.) and centrifuged similarly to obtain 490 g of the second wet cake and 497 g of the second mother liquor. The yield of the dry trimellitic acid was 410 g.

This trimellitic acid had a purity of 97.8% and a manganese content of 200 ppm.

The yield of trimellitic acid was 91.5%; the manganese loss, 1.6%; the water content of the first and second cakes, 21% and 19.5%, respectively; and the average particle size of the crystal was 66μ.

What is claimed is:

1. In crystallizing and separating trimellitic acid obtained by the oxidation of dimethylbenzaldehyde or its oxidation derivative with a molecular oxygen-containing gas in an aqueous solvent in the presence of a bromine ion or a bromine ion and a heavy metallic ion catalyst, the improvement which comprises carrying out the crystallization with at least two crystallization vessels connected in series, of which the first vessel is kept at a temperature of 40° to 130° C. and at a concentration of trimellitic acid of 20 to 60 wt. %.

2. In crystallizing and separating trimellitic acid obtained by the oxidation of dimethylbenzaldehyde or its oxidation derivative with a molecular oxygen-containing gas in an aqueous solvent in the presence of a bromine ion or a bromine ion and a heavy metallic ion catalyst, the improvement which comprises carrying out the crystallization with at least two crystallization vessels connected in series, of which the first vessel is kept at a temperature of 40° C. to 130° C. and at a concentration of trimellitic acid of 20 to 60 wt. %, and 10 to 50% of the slurry solution from the final crystallization vessel is circulated to the first vessel.

* * * * *